(12) United States Patent
Kranz

(10) Patent No.: US 6,762,419 B1
(45) Date of Patent: *Jul. 13, 2004

(54) ULTRAVIOLET LIGHT ILLUMINATION AND VIEWING SYSTEM AND METHOD FOR FLUORESCENT DYE LEAK DETECTION

(75) Inventor: Kenneth J. Kranz, Roseville, MI (US)

(73) Assignee: Corrosion Consultants, Inc., Roseville, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 515 days.

(21) Appl. No.: 08/964,839

(22) Filed: Nov. 5, 1997

(51) Int. Cl.[7] .............................. G01N 21/64; G01J 1/00
(52) U.S. Cl. .............................. 250/461.1; 250/504 R; 250/504 H
(58) Field of Search .......................... 250/459.1, 461.1, 250/504 R, 504 H, 302

(56) References Cited

U.S. PATENT DOCUMENTS

| | | | |
|---|---|---|---|
| 3,711,700 A | | 1/1973 | Westlund, Jr. et al. |
| 4,266,535 A | | 5/1981 | Moret |
| 5,421,192 A | * | 6/1995 | Henry .......................... 73/40.7 |
| 5,674,000 A | | 10/1997 | Kalley |
| 5,742,066 A | * | 4/1998 | Cavestri .................. 250/504 R |
| 5,816,692 A | * | 10/1998 | Cooper et al. .............. 362/293 |
| 5,905,268 A | | 5/1999 | Garcia et al. |

OTHER PUBLICATIONS

Kopp Glass Inc., "Color Filter Glasses", SL–5M–Feb. 1996.

* cited by examiner

*Primary Examiner*—Albert Gagliardi
(74) *Attorney, Agent, or Firm*—John R. Benefiel

(57) ABSTRACT

An illumination and viewing system and method for detecting leaks by observing material caused to fluoresce by being illuminated by a beam of ultraviolet light. The beam is concentrated by a parabolic reflector coated to maximize ultraviolet reflection, and then passed through a filter which reflects visible wavelengths while allowing transmission of ultraviolet and IR wavelengths. The fluorescing light is viewed through eyeglasses which block wavelengths just below the wavelengths of the emitted fluorescing light.

2 Claims, 1 Drawing Sheet

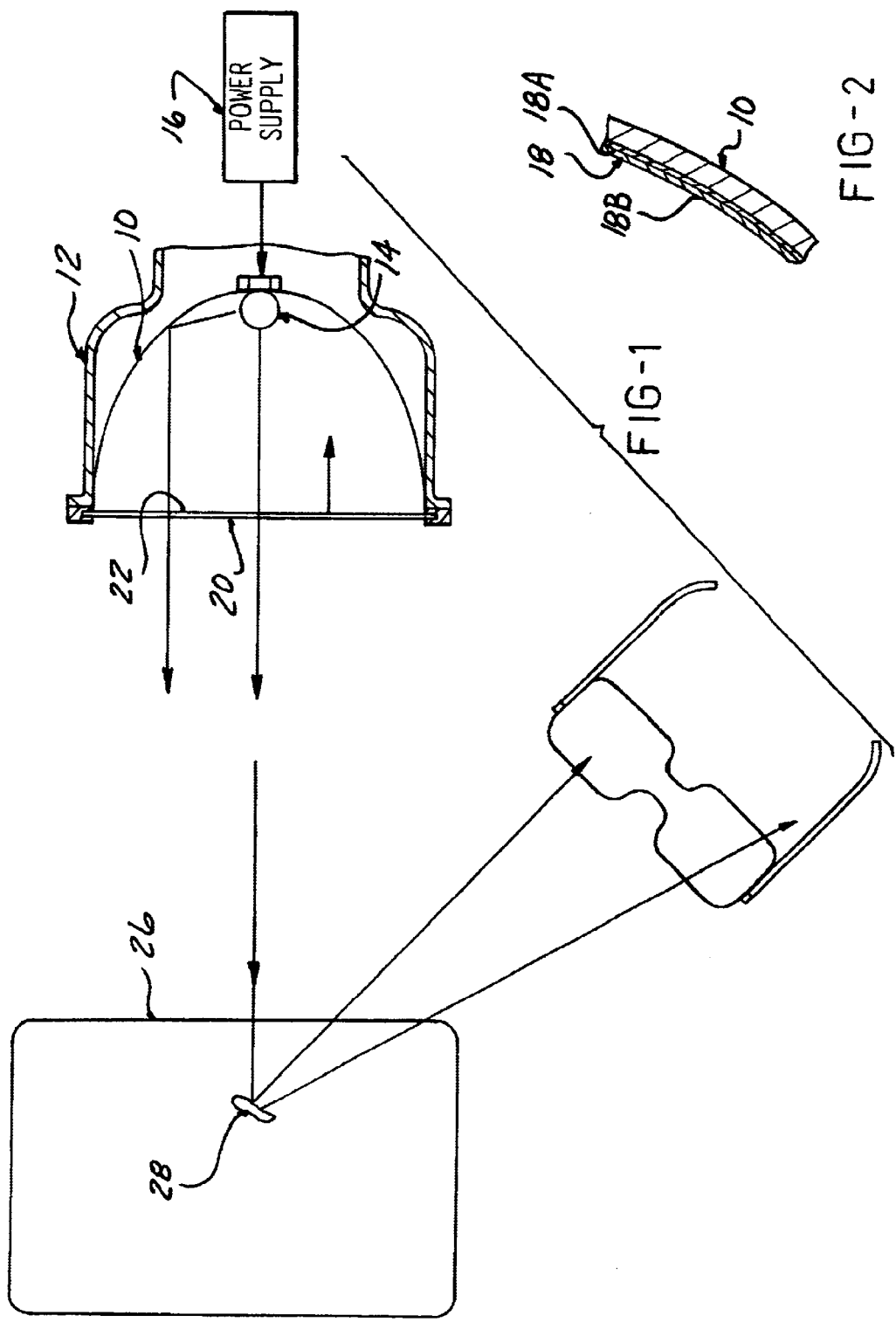

ULTRAVIOLET LIGHT ILLUMINATION AND VIEWING SYSTEM AND METHOD FOR FLUORESCENT DYE LEAK DETECTION

BACKGROUND OF THE INVENTION

This invention concern liquid leak detection methods and more particularly leak detection using dyes which fluoresce when illuminated by light of particular wavelengths, typically ultraviolet light, commonly referred to as "black light".

Ultraviolet light sources are commonly employed for such uses as disinfection, prospecting, document examination, dental work curing, as well as leak detection.

The fluorescing dye is typically mixed with lubricating oil which in turn is mixed with fluid in the equipment being inspected, such as in the refrigerant of an air conditioning system.

If a leak is present, the dye in the fluid leaked out will fluoresce when illuminated with ultraviolet light, so that the leaked fluid will be readily visible.

Such dyes will fluoresce or emit light at certain visible band wavelengths, when excited by shorter wavelength ultraviolet light.

In order to make such leak detection easy and reliable, particularly under bright light ambient conditions, a powerful light source emitting light at the proper wavelength should desirably be used, which source does not also emit visible light. If visible light is reflected from the surface being inspected, it will render the fluorescing light less conspicuous.

Currently available light sources are not of sufficient intensity and also emit significant visible wavelengths such that the contrast of the fluorescent light with the visible reflected light is not great enough for reliable observation.

An overheating problem is also encountered in attempting to eliminate visible light by absorption in a filter lens.

This overheating can crack or shatter the lens, particularly if water drops impinge on the lens, the shattered glass presenting a hazard to the user.

In attempting to create a more powerful light source, reflectors are commonly provided which concentrate and direct ultraviolet wavelength light emitted from a quartz envelope lamps. Prior art reflectors have typically been crudely formed and had low efficiency due to destruction interference set up by protective coatings such as silicon dioxide.

It is the object of the present invention to provide a system for ultraviolet light illumination of enhanced intensity for fluorescent leak detection to allow easier and more reliable viewing of fluorescent light emitted from a dye.

It is another object of the present invention to provide an ultraviolet light source which emits an intense ultraviolet beam directed through a glass filter so as to eliminate visible wavelengths but without producing heating of the glass filter.

SUMMARY OF THE INVENTION

The above objects and others which will become apparent upon a reading of the following specification and claims are achieved by a system comprised of an improved parabolic reflector and filter associated with an ultraviolet lamp, combined with viewing eyeglasses which filter certain visible wavelengths for achieving maximum contrast of the fluorescing light emitted from a dye exposed to the illumination by a leak.

The improved reflector has an accurately formed parabolic shape. Two coatings of precisely control thickness are applied to the reflecting surface and each have a substantially different refraction indices. These coatings minimize the interference of a reflected ultraviolet light beam with the incident light beam by inducing offsetting phase shifts such that the reflected light is closely in phase with the incident light. This result maximizes the intensity of the reflected ultraviolet light beam by minimizing destructive interference between the incident and reflected light beams which could otherwise occur. The ultraviolet light source is preferably a quartz envelop tungsten halogen lamp mounted at the focal point of the reflector parabola.

The ultraviolet light beam from the reflection is then passed through an optical filter to selectively remove visible light from the reflected light beam by a process of selective reflectance rather than absorbance so as to minimize heat build up in the filter, as has occurred in previous light absorbing filters used for removing visible light.

A series of coatings are applied to a borosilicate glass disc in order to achieve this. Successive coating layers of high and low refraction indices are used to produce selective reflectance of a wavelength band above the ultraviolet wavelengths but shorter than the infrared band, i.e., from 475 nm to 700 nm.

The infrared light is transmitted through the filter to reduce heating of the confined space behind the filter.

The final element of the system is a pair of filtering viewing eyeglasses which absorb wavelengths just below the wavelength of the fluorescing light in order to block wavelengths of the illuminating light in this band, to increase the contrast and visibility of the fluorescence of the illuminated dye to the viewer's eye.

The overall result is to produce an intense beam of ultraviolet light containing minimal visible wavelength light using practical components. The fluorescent light is thus strong and is not masked by the incidence of reflected visible light from the illuminating beam.

DESCRIPTION OF THE DRAWINGS

FIG. 1 is a diagram of the main components of the system according to the present invention.

FIG. 2 is an enlarged fragmentary section of the parabolic reflector component.

DETAILED DESCRIPTION

In the following detailed description, certain specific terminology will be employed for the sake of clarity and a particular embodiment described in accordance with the requirements of 35 USC 112, but it is to be understood that the same is not intended to be limiting and should not be so construed inasmuch as the invention is capable of taking many forms and variations within the scope of the appended claims.

The system according to the present invention uses a portable ultraviolet light source not unlike a flashlight, which includes a parabolically shaped reflector 10 mounted in a housing 12, (a portion only shown in fragmentary form) which in turn mounts a lamp 14 located approximately at the focal point of the parabolic shape.

The lamp 14 is preferably a Xenon lamp of high color temperature (>3500 K), which produces substantial long wave ultraviolet light emissions. The envelop is made of quartz which is itself highly transmittive to such long wave ultraviolet light.

The lamp 14 is also relatively compact allowing it to be placed at the focal point of the reflector parabolic shape.

A suitable bulb is available as part number FCR64625HLX from Osram Sylvania.

The parabolic reflector is precision electroformed of nickel on an accurately shaped stainless steel mandrel.

A focal point of 0.187 inches allows the lamp 14 to be approximately located at the focal point of the parabolic to maximize beam concentration.

The lamp 14 is powered by a suitable power supply 16 which may consist of a transformer reducing 110 V (or 220 V) to 12 V.

A 12 volt dc power supply such as an auto battery may also be used. The lamp 14 draws 100 watts of power such that a high power source will be required, substantially greater than that required for a typical flashlight. Preferably, a relay operated by a normally off spring biased switch (not shown) is used to turn the lamp 14 on and off, to minimize the on time of the lamp 14.

The reflecting surface 18 of the parabolic reflector 12 has a double layer of coatings, which are designed to eliminate the destructive interference caused by refraction of the interface of each media through which the light passes in being reflected from the surface 18. Refraction of short wavelength ultraviolet light would normally cause a phase difference to develop between the incident and reflective light beam, setting up a destructive interference and reducing the intensity of the reflected ultraviolet light.

The surface 18 is given coatings, one of aluminum and one of silicon dioxide. The interface of silicon dioxide and air, and silicon dioxide and aluminum produces a double refraction in an opposite sense, which offset each other to eliminate the potential destructive interference which otherwise could occur.

The first coating 18A is of aluminum, while the second coating 18B is of silicon dioxide (FIG. 2). The thickness of the silicon dioxide should be uniform and accurately held to achieve this effect, the thicknesses determined by the "quarter stack" principle.

The refractive index of each interface, i.e., the silicon dioxide and air, silicon dioxide and aluminum determines the effective phase shift of the reflected light. A thickness of aluminum of 0.057 microns and of silicon dioxide of 0.066 microns has been successfully used for this purpose. The silicon dioxide-air interface causes an approximate 13 degree forward phase shift, the silicon dioxide-aluminum interface a 13 degree lagging phase shift, thereby offsetting each other.

Silicon dioxide coatings have heretofore been employed simply to protect the substrate from scratches and oxidation but have not been sufficiently uniform nor of the proper thickness to achieve enhanced reflection of ultraviolet wavelengths.

A coated parabolic reflector suitable for this use is available from American Galvano, 312 N. Cota St., Unit I, Corona, Calif. 91720.

A glass disc filter 20 is another component of the system of the present invention which is mounted to receive the ultraviolet beam emanating from the lamp 12 and the parabolic surface 18.

The filter 20 is designed to reduce the visible light component of the ultraviolet light received from the lamp 12 and reflector 14.

Such filters have been employed in the past but have typically been designed to absorb visible light to prevent its transmittance. This results in excessive heating of the lens when used with high intensity light sources, making it vulnerable to cracking or shattering, as when contacted with water drops due to rapid cooling of localized areas of the glass.

According to the concept of the present invention, coatings are applied which cause reflection of the visible light ranges rather then absorbance, greatly reducing heating of the lens 20.

The filter 20 itself is preferably of borosilicate glass, commercially available as "Pyrex" (™), which has a very low coefficient of thermal expansion to thus minimize cracking from thermal shock.

The fluorescing dyes typically used for leak detection have an excitation range of ultraviolet light of wavelengths 320 nm to 475 nm. When excited by such ultraviolet light, fluorescing light of 495 to 500 nm is emitted.

It is thus desirable to allow maximum transmitting of the exciting wavelengths from 320 nm to 475 nm while reflecting wavelengths from 475 nm to 700 nm.

Light over 700 nm is in the invisible infrared range, which is allowed to be transmitted out of the confined space through the filter 20 to avoid overheating particularly of the reflector 14.

Particular coatings are applied to cause the filter 20 to reflect visible light above 475 nm and below 700 nm.

Using the "quarterwave stack" principle developed by H. A. Macleod, (See *Thin Film Optical Filters*, McGraw Hill 1989 ) two layers on high and low refractive indices may be stacked to cause reflection of wavelength s only from 475 nm to 700 nm, allowing transmission of wavelengths from 320 nm to 475 nm and 700 nm to 1300 nm.

The stack may be formed by the filter and a coating on the inside surface of the filter 20, which may be of titanium oxide.

The glass and titanium oxide are of a thickness necessary to reflect the wavelength ranges described.

Other coatings may be applied in various thicknesses, such as magnesium fluoride, which may also be applied to the other surface of the borosilicate to eliminate any residual transmitted visible lights.

The general methodology is to create a bandwidth of reflected light above 475 nm extending approximately to 700 nm. The mean wavelength around which this bandwidth is centered would be 537.5 nm and a reflected bandwidth of 225 nm should therefore be employed.

A suitable reflecting-transmitting filter lens for this purpose is available from:

Z, C & R Coatings for Optics, Inc.
1250 E. 223rd. Street
Suite 111
Carson, Calif. 90745

The system also involves the use of special viewing glasses 24 which are designed to absorb light wavelengths from 400 to 480 nm so that illuminating light from the source in those ranges reflecting from the inspected body 26 does not mask the emitted fluorescing light wavelengths which are in the 495 to 500 nm range emitted from the illuminated dye in the leaked liquid 28.

Such narrow band blocking eyeglass lenses are available from:

Noire Medical
6155 Pontiac Trail
South Lyon, Mich. 48178

Thus a powerful ultraviolet illuminating light source is provided, and the fluorescent light generated thereby is highly visible due to the minimization of reflected visible light, blocked by the filter 20 and absorbed in the eyeglasses 24.

This in turn makes leak detection inspections much easier and more reliable even at relatively brightly lit sites.

What is claimed is:

1. A system for illuminating an object with ultraviolet light, comprising:

a housing having an opening therein;

a high power ultraviolet lamp of a wattage much greater than a conventional flashlight mounted in said housing and when energized generating a beam of light containing ultraviolet, visible, and infrared wavelengths;

an optical element positioned to receive said beam of light and directing a great proportion of the ultraviolet light in said beam out of said housing through said opening and not directing a large proportion of longer visible band wavelength light in said beam out through said opening while directing a great proportion of infrared light wavelengths above approximately 700 nm out of said housing to minimize heating within said housing, said optical element having coatings selectively reflecting light of different wavelengths to cause said selective directing of said ultraviolet, and infrared wavelength light; out of said opening and reflection back of said visible wavelength light;

a parabolic reflector, said ultraviolet lamp disposed within said reflector located substantially at a focal point of said parabolic reflector;

said parabolic reflector having a reflecting surface coated to produce a double refraction in an opposite sense of ultraviolet light from said lamp so as to produce offsetting phase shifts in incident light from said ultraviolet lamp and to minimize destructive interference between an incident beam of ultraviolet light from said ultraviolet lamp and an ultraviolet beam reflected from said reflector.

2. The system according to claim 1 wherein coatings of silicon dioxide and aluminum are applied over a substrate forming said parabolic shape.

* * * * *

UNITED STATES PATENT AND TRADEMARK OFFICE
CERTIFICATE OF CORRECTION

PATENT NO. : 6,762,419 B1
DATED : July 13, 2004
INVENTOR(S) : Kenneth J. Kranz

It is certified that error appears in the above-identified patent and that said Letters Patent is hereby corrected as shown below:

Column 2,
Line 2, after delete "control" insert therefor -- controlled --.

Column 6,
Line 21, after "parabolic shape" insert -- , producing said double refraction --.

Signed and Sealed this

Fourth Day of January, 2005

JON W. DUDAS
*Director of the United States Patent and Trademark Office*